United States Patent [19]

Charlebois

[11] Patent Number: 5,230,339
[45] Date of Patent: Jul. 27, 1993

[54] PERFORMANCE EVALUATION OF ULTRASONIC EXAMINATION EQUIPMENT

[75] Inventor: Thomas F. Charlebois, Cleveland, Ohio

[73] Assignee: Array Tech, Inc., Cleveland, Ohio

[21] Appl. No.: 714,497

[22] Filed: Jun. 13, 1991

[51] Int. Cl.$^5$ .................... A61B 8/00; G01N 29/00
[52] U.S. Cl. .......................... 128/660.01; 73/1 DV
[58] Field of Search ........... 367/1, 13; 73/1 R, 1 DV, 73/3; 128/660.01, 660.07, 661.09

[56] References Cited

U.S. PATENT DOCUMENTS

| | | | |
|---|---|---|---|
| 3,921,121 | 11/1975 | Huisveld, Jr. et al. | 367/1 |
| 3,921,123 | 11/1975 | Early | 367/1 |
| 3,956,729 | 5/1976 | Epstein et al. | 367/1 |
| 3,959,766 | 5/1976 | Nees et al. | 367/1 |
| 4,194,167 | 3/1980 | Papineau | 361/1 X |
| 4,674,516 | 6/1987 | Hirota et al. | 128/661.01 |
| 4,694,680 | 9/1987 | Takeuchi et al. | 128/660.01 X |
| 4,719,509 | 1/1988 | Sakamoto | 128/660.07 X |
| 4,867,168 | 9/1989 | Stoor et al. | 128/660.01 X |
| 4,954,996 | 9/1990 | Fazzolari et al. | 367/13 |
| 5,095,910 | 3/1992 | Powers | 128/662.05 |
| 5,122,989 | 6/1992 | Pirie et al. | 367/13 X |

Primary Examiner—Francis Jaworski
Attorney, Agent, or Firm—Kevin J. Heyd

[57] ABSTRACT

A test system is disclosed for facilitating analysis and evaluation of medical performance of ultrasonic examination equipment, including ultrasonic imaging systems, Doppler ultrasonic systems and ultrasonic color flow mapping systems. The test system is employed while the ultrasonic examination system is operating. A test transducer apparatus is positioned at a location at which it receives incident ultrasonic energy from the examination system. Receiver and analyzer circuitry senses and identifies characteristics of the incident ultrasonic energy being produced by the examination system, and electronically produces signals representing these sensed characteristics. A storage device is provided to preserve representations of these characteristics. Synthesizer apparatus and circuitry utilizes the stored characteristic information to actuate the test transducer apparatus to propagate back to the transducer of the examination system apparent return echoes resembling ultrasonic echoes which would have been produced by the incidence of incident ultrasonic energy upon an acoustic image, had such an acoustic image been located within the examination system's field of view. The monitored characteristics of the incident ultrasound include wave shape, frequency, phase, signal duration, pulse duration and pulse rate. The location of the apparent acoustic interface represented by the false echoes returned can be adjusted by varying the time delay of the apparent return echoes relative to the occurrence of the corresponding incident ultrasonic energy. A moving acoustic image or point thereof can be simulated by changing the frequency of the apparent echoes relative to the frequency of the incident ultrasonic energy.

21 Claims, 3 Drawing Sheets

PERFORMANCE EVALUATION OF ULTRASONIC EXAMINATION EQUIPMENT

BACKGROUND OF THE INVENTION

1. Field Of The Invention

The invention relates generally to the field of ultrasonic examination, particularly to medical diagnostic ultrasonic examination. The invention relates more specifically to a system for facilitating the evaluation of performance characteristics of ultrasonic examination systems by electronic acoustic synthesis of static and dynamic structures within the ultrasonic system's field of view, rather than by placing a phantom tissue mimicking object in the field.

2. Background Art

Apparatus and systems are known for employing mechanical ultrasonic energy for non-invasive examination of internal body structure or condition of a patient or other subject. All of such system employ a transducer having at least one transducer element, along with transmitter circuitry, receiver circuitry, signal processing means and some type of display or other device for recording the results of the examination.

The transducer element or elements are often piezoelectric crystals which convert mechanical sound energy to electrical energy, and vice versa. In an examination, the transducer is placed upon the surface of the patient's body near the area sought to be studied. The transmitter is coupled to the transducer, and produces electrical signals which cause the transducer to propagate mechanical ultrasonic signals into the patient's body, either continuously or in pulses. The transmission period is relatively short in duration. Following the transmission period, the transducer is coupled to the receiver circuitry for a "listening" period many times longer than the transmission period.

Incident acoustic energy travels through body tissue at a high rate of speed.

Different organs and structures of the body have different acoustical impedances. Where a change in acoustical impedance occurs, an acoustical interface is defined. Incident ultrasonic radiation impinging upon an acoustical interface produces acoustic echoes which are reflected generally back toward the direction from which the incident ultrasonic energy originated.

The "listening" period is defined with sufficient duration to encompass the time at which an acoustic echo occurring in the region of interest will return to the transducer. Echoes striking the transducer cause the transducer to produce electrical signals which are representative of characteristics of those ultrasonic echoes. The electrical signals are transmitted from the transducer to the receiver, which often performs a buffering and/or amplification function. The electrical signals output from the receiver are transmitted to processing circuitry which sometimes includes means for digitizing the signals prior to processing. Storage means is often provided for preserving the signals. Some display device is included to present an image, histogram, or other tangible representation of the signals and of the location and intensity of the echoes that caused them.

The acoustic echoes, and hence the stored signals representing them, depend upon the physical properties of the acoustic interface or boundary which caused the generation of the echo signal. Such physical characteristics include the size of the boundary, the difference in acoustic impedance between the two media which define the boundary, and whether the interface happens to be in motion.

The stored electrical signals thus can be used to construct a visual image of the boundary, or to define in other ways one or more of the location or characteristics of the acoustic interface. This technique is generally referred to as ultrasonic imaging.

Other forms of ultrasonic examination exist. For example, the Doppler effect can be employed to detect and quantify motion of an acoustic interface or boundary. In ultrasonic systems for utilizing Doppler, a transducer propagates ultrasonic energy into the subject at a predetermined frequency. If an acoustic interface is in motion away from the ultrasonic source, the received ultrasonic echo frequency will be slightly lower than the transmitted frequency. If the ultrasonic interface is in motion toward the ultrasonic source, the received frequency will be slightly higher than that which was transmitted.

Such Doppler systems are often used to measure blood flow. The ultrasonic source directs incident ultrasonic energy along a blood vessel. Since blood is not a homogeneous fluid, but rather contains corpuscles which have acoustic impedance different from that of the surrounding fluids, ultrasound will be reflected from the blood corpuscles. If the corpuscles in the blood are moving away from the source, the return frequency will be lower than the incident frequency. If the blood if flowing toward the source, the return frequencies will be somewhat higher. The amount of difference between the transmitted and received frequencies indicates the velocity with which the acoustic interface is moving.

Another type of ultrasonic examination is known as color flow mapping.

Color flow mapping ultrasonic systems are a more sophisticated version of simple Doppler systems. Color flow mapping employs the Doppler effect to produce a multi-color display for simultaneously indicating various velocities of moving fluid which are distributed across the system's field of view. Color flow mapping systems substantially simultaneously observe and record the distribution of observed velocities across the field of view, and produce a display which indicates those different velocities in a predetermined color scheme.

It is necessary, from time to time, to evaluate and/or calibrate the performance of ultrasonic examination systems. It has been proposed to do this by placing a mechanical object, often called a "phantom", in the field of view of the ultrasonic examination system. The phantom is made of or contains a material which has an ultrasonic impedance resembling or mimicking that of body tissue of a particular organ or body structure.

To evaluate or calibrate performance, the examination system is operated with the phantom in the field of view. The image or other tangible representation of the phantom which is produced by the examination system is evaluated against an ideal image or other representation of the phantom which would be expected if the system were operating perfectly.

Other devices, or phantoms, used for testing performance of an ultrasonic Doppler system do so by mechanically moving an echogenic fluid within the field of view of the ultrasonic system. The moving field impresses a Doppler shift in frequency upon the ultrasonic signal transmitted from the ultrasonic examination system. This shift infrequency is then detected in the echo returned to the examination system.

Such Doppler phantoms, however, are very bulky. They require fluid pumps, motors and piping to create the fluid flow. In using them, it is very difficult to control the flow velocity of the fluid and they can only generate one Doppler shifted signal at a time. Furthermore, the flow that they do create is not a pure quantity that can be used for calibration purposes. This is due to the physics of the fluid flow in the rigid tubes of the phantom. Blood flow in an actual blood vessel exhibits somewhat different characteristics than fluid flow in a rigid tube, since blood vessels are somewhat elastic in nature.

For even in the case of simple laminar flow, the distribution of velocities across the rigid tubes is non-linear. The fluid in the center of the tube moves at a higher velocity than the fluid adjacent the tube walls. This makes it very difficult, if not impossible, to use the prior art Doppler phantom as an accurate means for calibrating Doppler systems.

Furthermore, to be able to generate multiple, simultaneous, calibrated Doppler shifts representing a plurality of velocities needed to accurately test color-flow imaging systems would be impossible to achieve with the prior art Doppler phantoms.

Examples of known types of ultrasound phantoms are described in the following United States Letter Patent, each of which is hereby expressly incorporated by reference: U.S. Pat. No. 4,843,866, issued on Jul. 4, 1989, to Madsen et al. for ULTRASOUND PHANTOM; U.S. Pat. No. 4,974,461, issued on Dec. 4, 1990 to Smith et al. for ANTHROPOMORPHIC CARDIAC ULTRASOUND PHANTOM.

It is an object of the present invention to provide apparatus and circuitry for evaluating the performance of an ultrasonic examination system which is compact, lightweight, and which does not require the placement of a mechanical phantom in the field of view of the ultrasonic system, and which is capable of the simultaneous generation of multiple simulations of both moving and stationary ultrasonic interfaces within the system's field of view.

DISCLOSURE OF THE INVENTION

The disadvantages of the prior art are eliminated or reduced by a test system for evaluating performance of an ultrasonic examination system by simulating an acoustic within the field of view of the ultrasonic examination system. The ultrasonic examination system includes ultrasonic transducer apparatus and a transmitter couplable to the transducer apparatus for actuating the transducer to propagate incident acoustic energy into the system's field. The examination system also includes a receiver couplable to the transducer for detecting electrical signals corresponding to ultrasonic echoes produced by the incidence of the transmitted acoustic energy upon acoustic interfaces within the field.

The test system includes a test transducer apparatus positionable to receive incident acoustic energy propagated through at least a portion of the field when the examination system is operated. An analyzer coupled to the test transducer senses characteristics of the received incident acoustic energy as defined by electrical signals produced by the test transducer. Information representing these characteristics is stored.

A synthesizer, coupled between the storage means and the test transducer apparatus, utilizes the stored characteristic information to actuate the test transducer to propagate acoustic energy back toward the transducer apparatus of the examination system. This returned acoustic energy emulates echoes which would have been caused if the incident acoustic energy propagated by the examination system had in fact encountered multiple acoustical interfaces.

This system facilitates calibration, quality control and performance testing of ultrasonic examination systems. It constitutes a unique electronic-acoustic test instrument which has the ability to quantify many aspects of the performance of acoustic imaging, Doppler studies and color flow mapping.

This system does not require the use of a tissue mimicking material or fluid to test acoustic imaging, color flow mapping or Doppler performance. The system overcomes the limited capability of the use of phantoms by electronically simulating to the ultrasonic examination system the presence of an acoustic image in its field of view.

This test system can facilitate the evaluation of many performance aspects of an ultrasonic examination system, such as sensitivity, directional discrimination, spatial resolution, contrast resolution, temporal resolution, acoustic signal to noise ratio, registration accuracy, velocity resolution and aliasing.

Characteristics of the acoustic energy which are analyzed include frequency, pulse shape, pulse repetition rate and phase of the incident sound wave. The simulator thus facilitates a complete and quantitative test of all imaging performance parameters of the ultrasonic examination system. The same stored characteristic information can be used repeatedly from day to day and performance data for the examination system can be compared between various ultrasonic examination systems available. This capability allows medical personnel to verify the operational integrity of their ultrasonic examination systems on a regular basis, as well as offering to a manufacturer of such equipment a practical test instrument for quality control and service.

This test instrument is applicable to facilitate evaluation of the performance parameters of all known types of medical ultrasonic examination systems. It is applicable to evaluating performance of ultrasonic imaging systems, which include Doppler, and color mapping capabilities.

In evaluating an ultrasonic imaging system, the test system simulates the presence of an acoustic image in the field of view by synthesizing a plurality of points. In order to emulate a stationary point, the system, in response to the receipt of an incident ultrasonic wave, synthesizes and returns a wave having shape, phase, frequency, pulse width and other characteristics substantially identical to those of the received incident acoustic energy.

The apparent location of the simulated point can be controlled by adjusting the time delay between the receipt of the incident wave and the return of the synthesized wave back to the transducer of the imaging system. The synthesized return wave can be made to resemble a point of an interface between acoustic media having various ratios of acoustic impedance by attenuating the simulated or apparent echo by an adjustable degree.

As mentioned above, an entire acoustic interface can be simulated by production of synthesized return waves corresponding to a plurality of points along the simulated interface. In order to do this, the test system, upon receipt of an incident wave, rapidly synthesizes and propagates a plurality of return waves during a single listening period of the ultrasonic imaging system following the period of transmission of the incident wave. This causes the ultrasonic imaging system to perceive an entire acoustic image interface. The shape of the apparent interface can be controlled by the apparent locations of the respective apparent points.

In addition to simulating stationary points and stationary interfaces, the test system can also simulate points and interfaces which are perceived by the ultrasonic examination system as being in motion. To do this, the system additionally slightly alters the frequency of the synthesized return, or simulated echo wave with respect to the frequency of the incident ultrasonic energy. If the frequency returned is greater than that received, a point is simulated such that the ultrasonic examination system perceives it to be moving toward its transducer. If the return frequency is less than the incident frequency, the point is perceived as moving away from the ultrasonic examination system transducer. The velocity of the apparent motion of the simulated point is dependent upon the absolute value of the difference between the incident and returned frequency.

An entire acoustic image interface motion can be simulated by producing a plurality of such apparently moving points, in a manner analogous to that described in connection with the stationery points and interfaces.

These and other aspects of the present invention will be understood in more detail by reference to the following specific description, and to the drawings, in which:

BEST MODE FOR CARRYING OUT THE INVENTION

Figure 1:
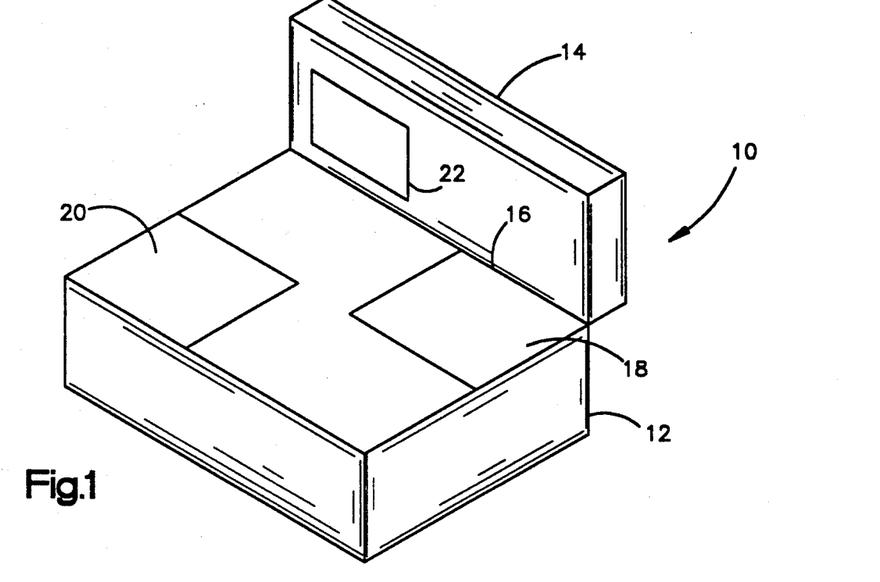
FIG. 1 is an isometric view illustrating a package incorporating the test system of the present invention.

FIG. 1 illustrates a preferred practical package configuration embodying the test system of this invention. The package and test system are indicated generally by the reference character 10.

The embodiment of the invention contained in the package is useful in testing performance of ultrasonic examination systems. It is operable without the need for conventional ultrasound phantoms.

The package 10 includes a base portion 12 and a lid 14. The lid 14 is hinged to the base 12 by known mechanical means along a line generally indicated at 16. Together, the base 12 and the lid 14 form a receptacle generally resembling a briefcase or small suitcase.

The base portion 12 contains, among other things, a test transducer apparatus generally indicated at reference character 18, a keyboard 20, and electronics comprising the test system, the electronics not shown in FIG. 1, but is discussed in more detail below. The electronics contained within the base 12 include a computer of the so-called PC variety. The lid portion 14 of the container package 10 includes a computer display 22, which is preferably of the liquid crystal type. In use, an operator raises the lid portion 14 of the package 10, and can then operate the keyboard 20 while viewing the display 22. Before beginning operation, the operator removes the test transducer apparatus 18 from the base 12 of the package, deploys the test transducer apparatus for use in testing an ultrasonic imaging system, and operates the test system via the keyboard while viewing the computer display 22.

The package 10 is designed to be small, portable and rugged, forming an instrument case for the easy transport and storage of the test system it contains. It is designed to minimize the weight of the package to facilitate its use as a service tool and to make it easy to handle for clinical personnel.

Figure 2:
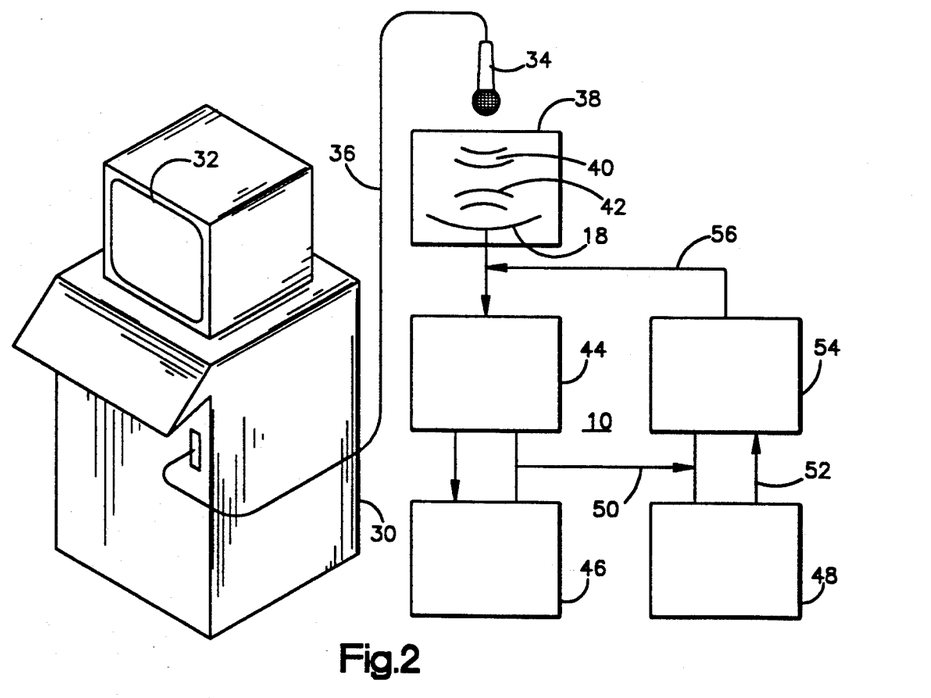
FIGS. 2 and 3 are generalized block diagrams illustrating the test system of this invention used in conjunction with an ultrasonic examination system.

FIG. 2 illustrates in block form a test system incorporating the present invention used in conjunction with an ultrasonic examination system 30. In the specific description, the ultrasonic examination system 30 is an ultrasonic imaging system. It is to be understood, however, that the present invention can be used equally well to test all modes of ultrasonic imaging, including Doppler systems, both continuous wave and pulsed, as well as ultrasonic color flow mapping, and the more traditional B and M mode imaging.

In FIG. 2, the ultrasonic imaging system includes internal electronics (not shown), a display monitor 32, and an ultrasonic system transducer 34 which is coupled to the system electronics by a cable 36.

Figure 3:
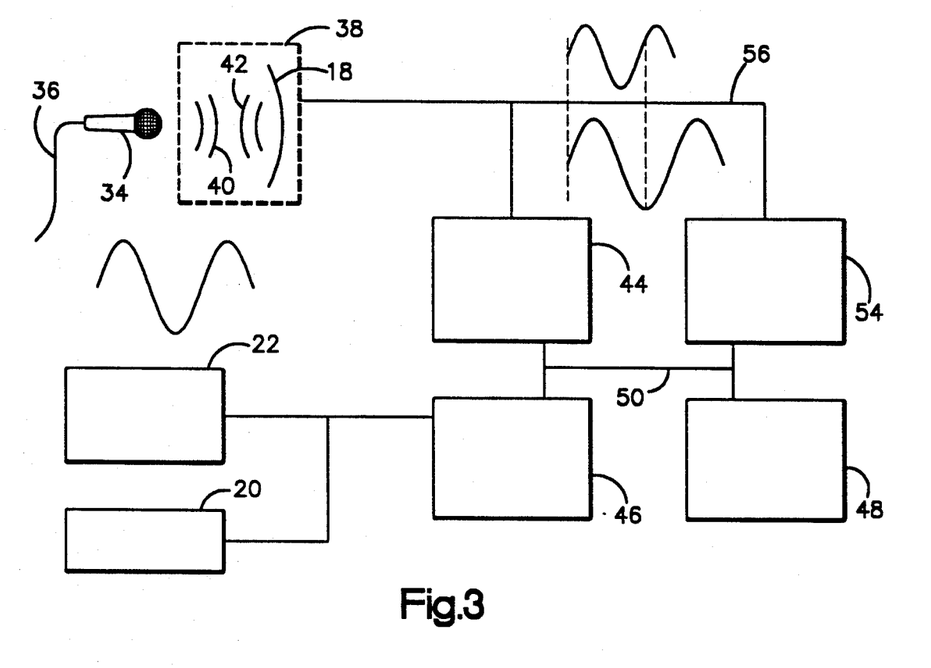

Major components of the ultrasonic performance test system 10 are illustrated in FIGS. 2 and 3. In FIG. 2, the ultrasonic test transducer apparatus 18 is illustrated as being located within the homogeneous medium chamber 38 and is disposed generally opposite the ultrasonic imaging system transducer 34. In operation, as will be described in more detail below, the ultrasonic imaging system 30 is operated without there being within the chamber 38 an actual object to be examined. Rather, what is in the chamber 38 is the test transducer apparatus 18, which interacts with the transducer 34 as described below.

More specifically, the test transducer apparatus 18 receives the incident ultrasonic energy 40 following its transmission from the transducer 34 through the chamber 38 until it reaches the test transducer apparatus 18. The incidence of the ultrasonic energy 40 on the test transducer 18 causes the test transducer 18 to produce electrical signals representing that incident acoustic energy.

The electrical signals from the test transducer apparatus 18 are transmitted to receiver and analyzer circuitry indicated by a block 44. The block 44 includes known receiver circuitry, and a known analog to digital converter for digitizing the received signals representing the incident ultrasonic energy 40. The block 44 also contains an analyzer which examines the signals corresponding to the incident ultrasonic energy to determine various characteristics of that incident ultrasonic energy. Among characteristics which are identified and quantified are frequency, phase, wave shape, pulse duration, length of pulse train and pulse repetition rate.

Digitized information indicating the characteristics of the detected waveform are fed to a digital computer 46, where that information is stored. The computer performs the function of a lookup table. In response to user actuation via the keyboard, the computer utilizes stored information defining the characteristics of the detected ultrasonic energy to generate and apply control signals which are used to synthesize apparent echoes 42 which are produced by the test transducer apparatus 18 and directed back toward the transducer 34 of the ultrasonic imaging system.

An important part of the test system is a digital waveform synthesizer 48. The synthesizer 48 receives control signals over a cable generally indicated at reference character 50 which extends from the computer to the synthesizer 48. In response to these control signals, the synthesizer 48 produces digital output signals over a lead generally indicated at reference character 52. These signals are directed to known transmitter and digital to analog converter circuitry generally indicated at the box 54. The data is converted to analog form, and then used to actuate the transmitter circuitry to produce analog electrical signals which are configured to cause the test transducer apparatus to produce the apparent echoes indicated at reference character 42. These electrical signals are transmitted to the test transducer apparatus 18 over a conductive path generally indicated as 56.

The simulator test system 10 is made up of a number of subsystems defined below and shown in FIGS. 2 and 3.

The Test Transducer Apparatus 18

The test transducer includes an acoustic array consisting of eight elements but may be expanded to a larger number. The material of the array itself is a polymer based piezoelectric because of its broad frequency response characteristics, but another piezoelectric material could also be used. The specific configuration of the array can vary. The preferred array is linear or curved but matrix array can also be used. The mechanical and electrical interface can remain constant, irrespective of the array configuration. The array is enclosed in an acoustic absorption material which has a similar acoustic impedance to soft tissue to minimize reflections within the acoustic chamber 38 of the system 10.

Although the preferred embodiment described herein places the test transducer array within the chamber 38, it is possible to build a working test system whose test transducer array is located outside the chamber 38 but acoustically coupled. It is even possible to build an operating system wherein the test transducer array is located anywhere within the acoustic field of view of the imaging system. The amplitude of the simulated waveform must be adjusted based on the acoustic beam profile response of the system under test. The acoustic response of the imaging system is based on its system parameters of phase or time delay accuracy, amplitude linearity between its transducer elements/electronics and the design of the imaging system's transducer. Therefore, the off axis acoustic performance of each system would be determined in the calibration mode by measuring the amplitude of transmitted beam at various angles within the imaging field of view. This would then allow amplitude correction for off axis simulation.

In practice, when the test transducer array is generally aligned with the transducer array of the imaging system, optimum results have been achieved when the two transducer arrays are separated by four to five centimeters.

As mentioned above, a variety of test transducer array configurations can be used. An annular array is possible, as well as a single element transducer.

Ultrasound System Transducer Interface

A variety of molds can be created to hold the most common transducers of each manufacture. The purpose is to simplify the operational use of the simulator test system 10 and eliminate the positional inaccuracies that might result from a general transducer holder. Note that a general holder might also be provided as a backup with detailed instructions on its use and limitations. The molds should all have a common outside geometry to fit into a holding fixture that will interface the imaging system transducer 34 to that of the test system 10. Each simulator preferably has a family of basic molds along with a general mold with optional molds available. These female molds should be made out of a soft material like RTV to protect the transducers.

Simulator Test System Electronics

The electronics are embodied on standard sized PC boards and format so that they plug into the slots of the PC computer mother board. The general functions of these boards will be described herein.

The boards together comprise a complete set of acoustic receivers, transmitters, and the signal processor circuitry for eight array elements. Additional transducer elements may be added to the test system by adding another PC board for each additional 8 element groups.

The individual transmitters and receivers 54,44 are separately connected to respective transducers of the array and may be individually operated or operationally grouped in any configuration.

The synthesizer 48 is a TMC2340 Digital Waveform Synthesizer. This device automatically generates 16-Bit sine waves which may be phase and amplitude modulated on the chip as desired.

The digital synthesizer chip designated TMC2340 is manufactured by TRW LSI Products, Inc. of La Jolla, Calif., USA. A full description of the chip function, its operations, applications, and interfacings, is set forth in a 13 page publication identified as TRW, Inc. publication 40G08770 Rev. A July 1990, which is hereby expressly incorporated by reference.

Operations performed by the above identified TRW chip, and which are achievable with such a chip by one of ordinary skill in the art, include the functions described in a publication entitled "Create Signals Having Optimum Resolution, Response, And Noise," *Electronic Design News* Mar. 14, 1991, pp. 87 et. seq.

This waveform synthesizer is coupled with a D to A converter to provide accurate waveforms, at frequency resolution better that 1 Hz, over the frequency range of interest (1-10 MHz).

The receiver circuitry 44 amplifies the signal detected by the test transducer array 18 and digitizes it to an 8-bit digital signal which is transferred to the computer 46 for storage. The receiver 44 is programmed in known fashion to accept "n" sample pulses from the ultrasound system transducer 34 to calibrate the test system 10. The samples which are processed in known fashion by the computer 46 to determine amplitude, pulse shape, and frequency of the detected waveform. In addition the receiver determines in known fashion the PRF of the ultrasound imaging system's current operating mode and transfers this information to the computer 46.

The transmitter circuitry 54 of the test transducer array 18 is capable of driving any element of the array 18 with a waveform up to 5 volts in amplitude. The magnitude of the simulated, or emulated, pulse is controllable in 1 dB increments over a dynamic range of >60 dB. The specific waveform 42 transmitted by the test system 10 is determined by the detected ultrasound waveform 42, and by operator test selection via the keyboard 20.

The PC computer 46 is an Intel 286 based mother board.

The display 22 is a small LCD of the known type used in portable computers.

The display is an LCD dot matrix module designated AND711AST.

The operator interface to the test system is through a standard PC computer keyboard. The function keys provide the selection of the various tests to be performed and very simple menus prompt the operator as required for appropriate input.

While those of ordinary skill in the art will be able to implement the functions described above, particularly in view of the incorporated subject matter, the following detailed flow description is provided for the benefit of those not intimately familiar with this art:

Flow Diagram for Simulator

01) Power On
Computer is initialized with an Autoexec Batch File to display Operator Prompts 02) Select System Type
A table of System types is displayed Operator enter code from table Push "Enter Key"

03) Input Transducer Frequency MHz

04) Select Test Mode
A table of different test modes is displayed Operator enters code from table Push "Enter Key"

05) Computer Initiates Calibration Program
A menu of system set-up conditions is displayed Operator sets controls on system as instructed Push "Enter Key" (starts Simulator Calibration)

06) Simulator detects Image System Transmit Pulse

07) Detected Pulse is digitized and stored in simulator memory as pulse data

08) Pulse data is transferred to the computer memory

09) Simulator detects next Image System Transmit Pulse

10) Sequence #07 through #09 is repeated "n times" Note "n" is dependent on System 10) Simulator counts time between Pulses and Stores digital data as Pulse Repetition Rate Data (PRF)

11) PRF data (time between pulses) is transferred to computer

12) The computer Averages the pulse data samples

13) The computer calculates the zero crossing points of the averaged pulse data by using a cosine interpolation 14) The Pulse center frequency (Fc) is calculated from the zero crossing times (T)
$Fc = \frac{1}{2}T$ 15) The number of zero crossings of the averaged pulse data defines the length of the simulated pulse 16) The Amplitude of the averaged pulse data is used to modulate the amplitude of the simulated pulse 17) The PRF is calculated by the computer as the reciprocal of the time between pulses 18) The PRF rate is used to determine the specific test pattern within the selected test
For example in B-Mode it equals the max imaging depth In Doppler-Mode and CFM Mode it defines the alias frequency 19) The above Pulse frequency Fc, Pulse Length, PRF and Pulse Amplitude Modulation Data are stored in the Computer Memory to be used for the simulation test 20) The computer prompts the operator to select the specific test pattern for the selected mode from a table Push "Enter" (Calibration Complete)

21) The Computer loads the memory table of the simulator with a specific test pattern 22) The simulator detects the Image System pulse and sequentially generates the defined test pattern from its memory 23) The simulator detects each ultrasound beam from the imaging field of view and generates a specific test pattern sequence for each imaging line at a synchronized time Note: because the simulator can generate any frequency or amplitude it is possible to simulate the echoes that would be seen by the system if stationary or moving objects were in the imaging system's field of view 24) The test continues until the operator stops the test or selects a new test.

Figure 5:
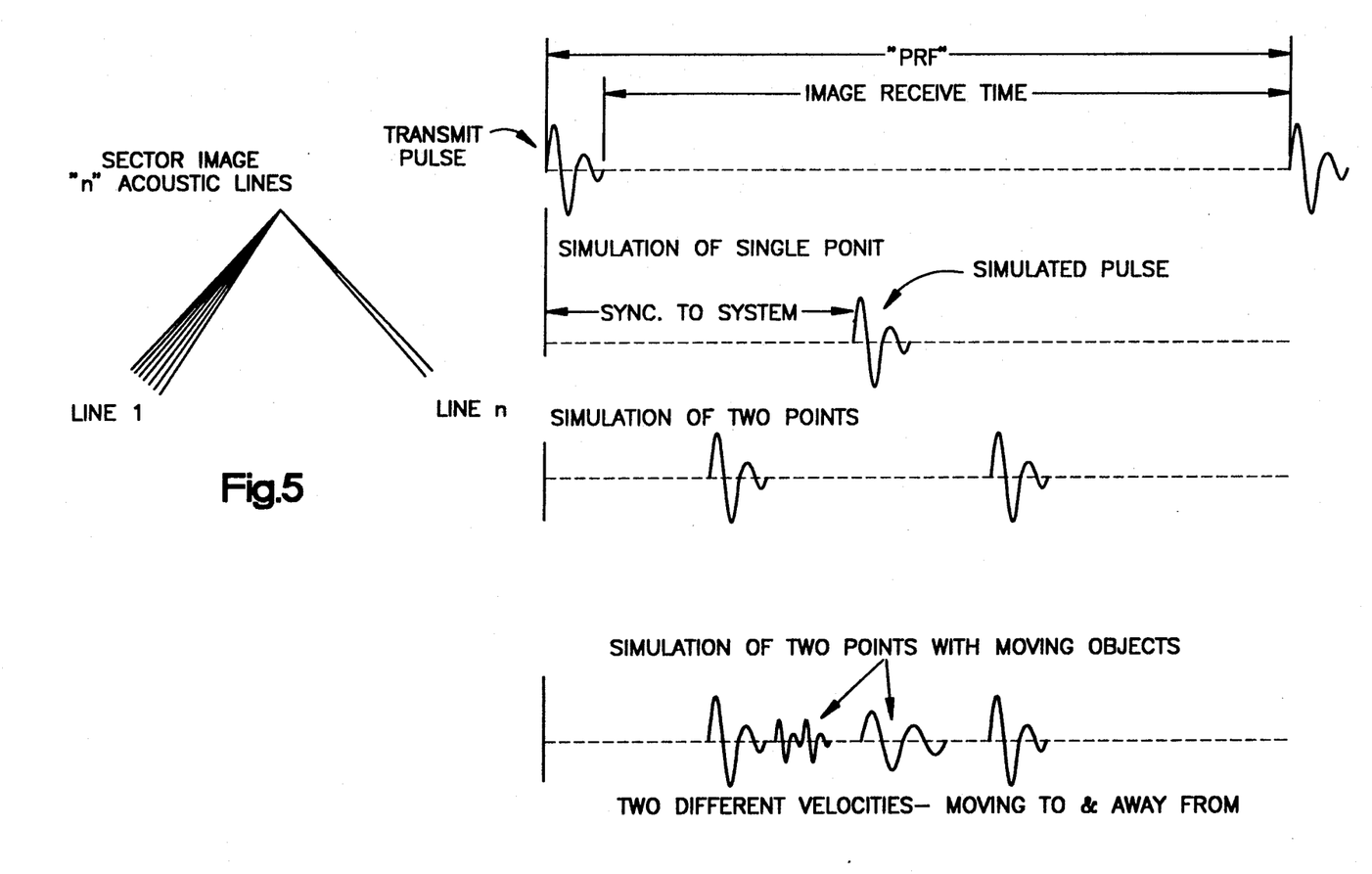
FIG. 5 is an illustration depicting timing details of a flow chart described in the present specification.

Reference FIG. 5 for timing details.

Detailed Theory of Operation

The operating principal of the above described test system is as follows:

An ultrasound imaging system has several basic modes; acoustic imaging, which includes B-mode and M-mode, Pulse and CW (continuous wave) Doppler and CFM (Color Flow Mapping). Each of these operational modes may be evaluated by use of the test system as described below.

B & M Mode Acoustic Imaging Test

B-mode Imaging, or brightness mode imaging typically produces black and white images of structures which have different acoustic impedances. Basically the ultrasound imaging system transmits a short pulse of electrical energy to its transducer. The transducer converts this electrical energy to mechanical energy in the form of an incident sound wave which is transmitted into the object being imaged. As this sound wave travels through the object, part of the sound wave is reflected at each acoustic boundary back to the transducer. The propagation of sound, its reflection and attenuation is a physical phenomenon which is described in most basic physics books. Simply stated the sound reflected is proportional to the ratio of acoustic impedance and the angle of incidence.

The sound returning is detected by the transducer and processed by the ultrasound imaging system. In B-mode imaging the amplitude of the returning echo is displayed as a proportional level of brightness to indicate the acoustic impedance difference of the boundary. An acoustic image is formed by mapping all of the acoustic boundaries over an area of interest. The quality of the resultant image is measured by its spatial, contrast and temporal resolution. These image quality parameters are dependent on the characteristics of the transmitted ultrasound beam such as frequency, the acoustic beam shape and pulse shape. The characteristics of the transducer and the imaging system's electronics also greatly affect the quality of the image since ultrasound imaging is a pulse-echo dependent technique.

Therefore the test system detects the actual ultrasound wave with its broad band frequency (0.1 to 10 MHz) elements and analyzes them to determine the respective frequency and pulse shape as well as the beam profile of the transmitting transducer. In the B &

M mode test the spatial and contrast resolution of the imaging system are tested by returning to the imaging system transducer a sequence of sound waves which emulate the detected incident sound waves (apparent echoes) at precise times and amplitudes, creating an apparent image, which resembles an image which would have been produced by the imaging system had a test object of particular characteristics actually been present in the imaging system's field of view.

This simulated image is actually processed and displayed by the ultrasound imaging system in response to the simulated or apparent echo sound waves, because the timing and amplitude of the simulated echo sound waves is controlled very accurately by the test system. Hence repeatable apparent images constituting test patterns may be created, which test the imaging capability of the ultrasound imaging system.

Previously, when it was desired to determine the spatial resolution of an ultrasound imaging system, a phantom having one or more test objects in a specific medium, the objects having a known spatial relative orientation, was used. Images of the object were taken using the ultrasound system, and the resultant image was analyzed to determine the resolving power of the imaging system. It is extremely difficult to select material and objects which test the entire dynamic range of spatial and contrast resolving power of an ultrasound imaging system. The present test system, however, can do this, and with accuracy and precision greater than that of the imaging system under test. Hence by creating specific ultrasound test images, by generating simulated or apparent echoes, the spatial and contrast resolution performance of an ultrasound image system can be quantified.

To measure temporal resolution of an ultrasound imaging system, a specific set of dynamic test images with controllable sequence times (frame rate) are created. The ability of the system to accurately track and display the moving test images is directly viewable on the ultrasound imaging system's monitor. Hence this test is used to determine the temporal resolution of B-mode and M-mode by accurately simulating structures with motion.

Pulse and CW Doppler Test

In both Pulse and CW Doppler the ultrasound imaging system looks for a shift in the frequency of the returning sound waves. The Doppler frequency shift is defined by the equation:

$$fs = V \cdot 2fo \cdot \cos\theta / c$$

where
fs = Doppler frequency shift
V = Velocity of object or fluid
fo = frequency of interrogation (incident frequency)
0 = angle of incidence
c = velocity of sound or the velocity of the moving object or fluid:

$$V = (fs \cdot c)/2fo \cdot \cos\theta$$

Hence, when the sound wave intercepts a moving object or fluid the frequency of the reflected sound wave is changed to be higher or lower than the transmitted sound wave used to interrogate the medium, the amount of charge being dependant on the direction of the motion. It is this principle that an ultrasound imaging system uses to calculate the velocity of moving objects or fluids. Therefore, to test the Doppler capability of ultrasound imaging systems, the test system creates calibrated frequency shifts relative to the original waveform, in order to emulate the sound patterns that would have been reflected by moving objects or fluids. Since the test system can accurately synthesize all frequencies and wave shapes, a new sound wave is created which corresponds to any desired test pattern based on the interrogating (detected) sound wave.

The test system can generate a range of frequency shifts to calibrate the imaging system as well as determine the alias frequency. It can evaluate the Doppler sensitivity by accurately attenuating the echo emulating sound wave in 1d B increments to determine the threshold of detection. In addition, a specified noise pattern may also be created with the shifted frequency sound waves.

Color Flow Mapping—"CFM"

In the simulation of CFM the principle is the same as that of Doppler. The interrogating, or incident, sound wave is modified infrequency as desired to generate the appropriate reflected sound waves. The ultrasound imaging system uses a different processing technique for color but the physical phenomena that is being evaluated is the same as in the Doppler case. The ultrasound imaging system, in color flow mapping, is looking for average velocity of matter in motion and not the complete spectrum of velocities as is evaluated by pulse and by CW Doppler modes.

The CFM image, by contrast, is an average velocity map of the region of interest being interrogated. In order to simulate a color image the apparent echo sound waves created by the test system must cover a range of spatial and temporal positions as well as a range of velocities. While this is more demanding it is a simple extension of the capability of the test system discussed above.

An important aspect of the evaluation of CFM is that, in acoustic imaging, color is used as an overlay of velocity to the structural image being shown in Black & White (B&W). It must be remembered that the color information without the B&W Image is not very useful. Therefore it is important to evaluate the imaging system's performance of the combined mode—B&W with Color. This specifically evaluates the imaging system's processing integrity of the combined imaging mode. The CFM sensitivity of an ultrasound imaging system is determined by controlling the amplitude and shape of the simulated waveform to determine the imaging system's threshold of detectability.

Summary

The unique test system capability to create sound waves which emulate dynamic structures with variable contrast allows the creation of apparent anatomical like structures with motion(like the Heart). Coupled to this is the ability to continuously modify the frequency of the returning sound waves so as to emulate complex flow patterns within the above anatomical structures. This capability is considered useful to train new physicians and technologists in interpretation of acoustic images.

SIMULATOR TEST SYSTEM CALIBRATION PROCEDURE

The imaging system 30 is initialized in known fashion in one of its standard imaging modes (B&W Imaging, Doppler, CFM) and its transducer 34 is placed on the simulator's image interface area 38. Alignment of the two arrays 34 and 18 is achieved by a simple fixture (not shown) which positions and holds the image system transducer 34 in place throughout the test. The operator is able to visualize the test transducer array 18 on the imaging system's video display monitor 32.

The operator then selects a calibration mode function key on the simulator's keyboard 20. The operator then enters an indication of the image system current operating mode. This mode is elected via the keyboard 20 in response to prompts from a simple computer menu displayed on the simulator's display 22.

The piezoelectric elements of the test transducer array 18 receive the incident sound wave from 40 transmitted from the imaging system's transducer 34. This sound wave is converted from acoustic energy to electrical energy by the array 18. The electrical energy is then buffered by an amplifier 60 (see FIG. 4) in the receiver 44. The output of the amplifier 60 is connected to a threshold circuit 62 and to an A to D converter 64 in parallel. The threshold circuit 62 detects the start of a pulse sequence and triggers the start of a counter 66 which counts the time to the next pulse sequence, which is the time to the next trigger pulse to the counter 66. This time is counted in 40 nanosecond increments and the digital number (the pulse Repetition Time—"PFR") is stored in a memory buffer 68 for transfer to the computer.

Figure 4:
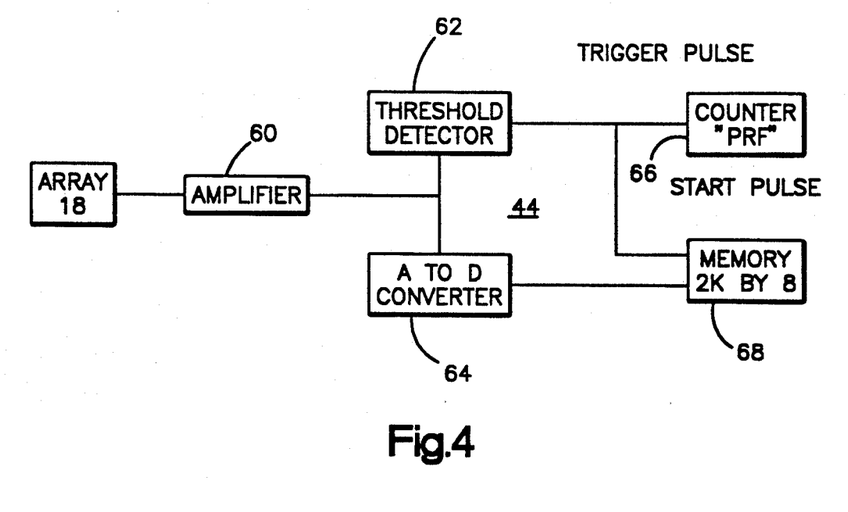
FIG. 4 is a block diagram illustrating a detail of the system of FIGS. 1, 2 and 3.

In parallel to this the A to D converter 64 is also receiving the buffered electrical signal and is digitizing this signal at 25 million samples per second. However, since the pulse from the imaging system is normally very short in duration (except in continuous wave) only a few samples need to be recorded to reconstruct the received waveform consistent with the Nyquist rate of sampling theory. The typical pulse length in imaging modes is several cycles at the frequency of imaging, but in pulse Doppler mode the pulse train length may be up to 3 to 4 micro seconds in length. The start pulse signal from the threshold circuit is used to initiate the memory of the A to D converter to save up to 2000 samples of the received signal.

The output of the PFR Counter 66 (a digital number) is read by the computer and then used in its calculations as well as shown to the operator on the simulator's display 22. The digitized signal memory 68 is read by the computer and the information is used to calculate the center frequency of the received pulse by looking at zero crossings of the waveform. The digital samples of the transmitted incident waveform 40 were taken at 25 million per second which is well above the Nyquist sampling rate for the waveforms being evaluated. However, to improve the accuracy of the recorded waveform many samples of the waveform may be averaged.

For example, a typical imaging frequency is 2.5 MHz, which has a period of 40 nanoseconds and a typical pulse length of 3 cycles or about 1.2 micro seconds. The digitized samples would be taken every 40 nanoseconds or 10 samples per cycle, which is 5 times higher than the Nyquist limit. The system may select to average 10 (or 1000) samples of incoming waveform 40 to minimize noise, since real time operation is not necessary during calibration.

The center frequency of the received pulse is calculated by the computer which determines the time period between the zero crossings, of the digitized signal. This is done by expanding the number of data points between the digitized samples using a sine function interpolation to refine the zero crossing accuracy. Once the center frequency is determined the pulse shape is evaluated by looking at the number and amplitude of each cycle. This information is stored in the computer and also shown to the operator on the simulator display 22.

In B&W Imaging, the frequency synthesizer 48 is controlled by the computer 46 to generate the specific frequency and waveform which emulates the received signal, at very specific times. However, this must be synchronized with the imaging system operation, since the transmitted ultrasound beam is constantly being steered throughout the imaging plane of interest. Therefore, it is necessary for the simulator test system to know the complete characteristics of the incident transmitted waveform and to understand the movement of the ultrasound beam over time. The incident transmitted beam shape is determined by operating the imaging system in known modes while calibrating and learning the operating sequence of the system. This is why a complete array of elements is required by the simulator test system to sense the transmitted beams characteristics at all angles within the imaging plane. That is, the signal of each element of the test transducer array 18 is digitized and stored by the computer 46 to know the beam shape characteristics.

The frame rate of the imaging system is also detected by the simulator test system by tracking the motion of the ultrasound beam as it moves across the image plane.

Once the simulator test transducer has calibrated itself on the imaging system, it is then capable of generating the specific waveforms, at the precise times necessary to generate desired test patterns.

BLACK AND WHITE SIMULATED STATIONARY IMAGE GENERATION

When a black and white ultrasound image is required it is necessary to generate a sequence of individual stationary simulated targets at various points in space or specifically generate simulated waveforms at very precise times relative to operation of the imaging system under test. A simple, one point stationary target emulation or simulation is generated by transmitting a single simulated waveform 42 from a specific element of the test transducer array at a precise time relative to the imaging system's operation and continue to repeat this waveform at the same precise times relative to the timing of the successive incident pulse waveforms from the imaging system. Each element in the test transducer array 18 is a point source receiver and transmitter at the depth, size and frequency range of the simulator test system. To construct a complete stationary image, a multitude of simulated waveforms 42 are transmitted at precise times from specific point sources dependent on the parameters of the imaging system under test.

To create a simulation of a stationary point, the returned waveform 42 has the same shape and frequency as the incident waveform 40. Different types of acoustic interfaces can be simulated by altering the amplitude of the returned waveform 42.

The actual simulated waveform is created by the digital frequency synthesizer chip TMC2340 (TRW), at reference character 48. This chip is initialized by the computer 46 to tell it what frequency and amplitude sinusoid to generate. The digital synthesized waveform may be frequency, phase and amplitude modulated to emulate the imaging system's incident transmitted waveform 40 which was received and analyzed during the calibration mode described above. The synthesized digital waveform is converted to an analog waveform by a TRW companion D to A converter TDC11012. The analog waveform is amplified by the transmitter 54 which can adjust the amplitude of the returning signal by 100 dB in 1 dB increments to emulate image points of different acoustic impedance. This analog waveform is switched to the appropriate element of the simulator test transducer array 18 and the simulated waveform 42 is converted to acoustic energy by the piezoelectric element.

This simulated waveform 42 is then received by the ultrasound imaging system 30 via its transducer 34, processed and displayed as an image point on the imaging system display 32. An ultrasound image is created by the imaging system one point at a time, so it is only necessary to synchronize with the imaging system 30 under test and return individual image points one at a time. However, if it is desirable to generate acoustic noise in addition to the desired image multiple transmissions of waveforms are possible by using other elements of the simulator test transducer array 18 simultaneously with the selected simulated waveform.

DOPPLER SIMULATED IMAGE GENERATION

In both pulse and continuous wave Doppler the imaging system 30 is looking for a very precise frequency shift in the returning waveforms (or simulated waveform 42). It is necessary for the operator to select the Doppler test mode of the simulator test system by pushing a defined function key on its keyboard 20 and then follow a defined calibration procedure outlined on the simulator display 22. This procedure is the same as defined above but must be repeated because the imaging system's imaging parameters change for Doppler Imaging. For example, the PRF and image frame rate are different in the Doppler imaging mode and must be learned by the computer.

The PRF in pulse Doppler defines the highest frequency that can be detected by the imaging system before aliasing occurs. The computer 46 calculates this point as well as the center frequency of the transmitted waveform 40 so the desired operated selected test patterns can be created. The pulse length of the transmitted waveform 40 must also be determined during the calibration procedure to ensure the appropriate length and shape of the simulated waveform 42. Based on the above information the computer initializes the synthesizer chip 48 to generate the desired waveform at the specific frequency shift to correspond to a moving target with velocity and direction at a specific point in space.

In the Doppler test mode it is desirable to quantify the imaging system's accuracy at detecting various velocity shifts. Since the synthesizer chip of the test system can accurately increment frequency shifts of 1 Hz, this is far beyond the resolution of the test, which is on the order of 10 Hz in the most accurate ultrasonic imaging systems. Therefore, the accuracy of the imaging system 30 to detect and display velocity information is established by using the simulator test system to accurately generate a known velocity and observing the imaging system's displayed velocity information on its monitor 32.

The Doppler sensitivity is measured by quantifying the minimum threshold of detectability of a Doppler signal by accurately controlling the amplitude of the transmitted simulated waveform 42. The Doppler sensitivity is thus obtained by observing the minimum signal which is detectable on the Image system monitor 32 and the amplitude of the test system's signal which is displayed for operator viewing on its monitor 22.

It is possible to generate a static image and a Doppler image simultaneously on the imaging system 30 with the test system, since the ultrasound image is formed one point at a time. It is therefore only necessary to synchronously generate a simulated signal which corresponds to a point on a static or moving acoustic interface one at a time.

An important aspect of Doppler simulation is that the simulated waveform 42 should have a waveform shape substantially identical with that of the incident waveform 40, but a frequency which is displayed from that of the incident waveform. The amplitude of the simulated waveform 42 can also be adjusted to simulate different acoustic impedance ratios of the type of acoustic interface which is to be simulated.

COLOR FLOW IMAGE SIMULATION

In a manner similar to Doppler Imaging, the ultrasound image system is looking for a frequency shift of the returning echoes. However, the system is evaluating a complete region of interest for average velocity information which in turn corresponds to an average velocity map. The system is looking for the frequency shift in the echoes which return, but in a variety of signal processing techniques. However, it is not important to the simulator test system which approach is being utilized to detect average velocity, only that all systems are looking for the same physical phenomena which is a corresponding shift in the frequency of the returning echoes representing a relative velocity for the particular region of interest. Hence, the simulator test system is calibrated in the same manner as described above, and then it is only necessary that the simulator test system generate frequency shifted sound waves at the appropriate time to emulate moving acoustic structures.

In the same manner as above, it is relatively simple to sequentially and synchronously simulate stationary and moving acoustic structures. It is therefore a simple task for the computer to sequentially modify the digital waveform synthesis to emulate the desired waveform. This sequence of simulated waveforms is combined to generate repeatable and dynamic test patterns which may be simple or complex in nature but most importantly the sequence may correspond to dynamic acoustic representation of anatomical images or test patterns.

I claim:

1. A method for evaluating performance of an ultrasonic examination system by synthesizing the presence of an acoustic image within the field of view of the ultrasonic examination system, the system having ultrasonic transducer apparatus, a transmitter for actuating the transducer apparatus to propagate incident acoustic energy into the field of view and a receiver for detecting ultrasonic echoes produced by the incidence of said incident acoustic energy upon acoustic interfaces within the region, said method comprising the steps of:

a) operating the ultrasonic system;

b) detecting characteristics of said incident acoustic energy;

c) utilizing said detected characteristics to synthesize apparent acoustic echo energy similar to said incident acoustic energy and propagating said apparent echo energy back toward the transducer apparatus of said system in response to said detection of said incident acoustic energy.

2. The method of claim 1, wherein said step of detecting characteristics of said incident acoustic energy comprises detecting wave shape, amplitude, and frequency of said incident ultrasonic energy.

3. The method of claim 1, wherein said step of synthesizing apparent acoustic echoes comprises:

returning such apparent echoes with wave shape similar to that of said incident acoustic energy, but with the frequency of said apparent echoes altered from that of the incident acoustic energy, to emulate an acoustic interface point which is in motion.

4. The method of claim 1, wherein said step of synthesizing and returning apparent echoes comprises:

returning said echoes at a time delayed by an adjustable amount following generation of said incident acoustic energy.

5. The method of claim 1, wherein:

a) said ultrasonic system includes means for propagating said acoustic energy during a transmission period and for coupling its transducer apparatus to the receiver for a listening period longer than said transmission period; and, b) said step of synthesizing and returning an apparent echo comprises returning a plurality of said false echoes during said listening period.

6. The method of claim 1, wherein said ultrasonic examination system is an ultrasonic imaging system.

7. The method of claim 1, wherein said ultrasonic examination system is an ultrasonic Doppler system.

8. The method of claim 1, wherein the ultrasonic examination system is a color flow mapping system.

9. A test system for evaluating performance of an ultrasonic examination system by emulating the presence of an acoustic image within the field of the ultrasonic examination system, the ultrasonic examination system having ultrasonic transducer apparatus, a transmitter for actuating the transducer apparatus to propagate incident acoustic energy into the field and a receiver for detecting ultrasonic echoes produced by the incidence of said incident acoustic energy upon acoustic interfaces within the region, said test system comprising:

a) a test transducer apparatus positionable to receive incident acoustic energy propagated through at least some of the field by the ultrasonic examination system;

b) an analyzer coupled to the test transducer apparatus for identifying characteristics of said incident acoustic energy;

c) storage means for preserving information representing said identified characteristics;

d) a synthesizer coupled between said storage means and said test transducer apparatus for utilizing said preserved information to cause said test transducer apparatus to propagate an apparent acoustic image the transducer apparatus of said ultrasonic examination system, the apparent echo being similar to said incident acoustic energy.

10. The test system of claim 9, wherein said analyzer and storage means include means for identifying and storing characteristics of said incident acoustic energy including acoustic wave shape, amplitude and frequency of said incident ultrasonic energy.

11. The test system of claim 9, wherein said synthesizer comprises circuitry for propagating said apparent acoustic image having characteristics similar to that of said incident acoustic energy, but having a frequency differing from that of said incident acoustic energy.

12. The test system of claim 9, wherein said ultrasonic examination system comprises an ultrasonic imaging system.

13. The system of claim 9, wherein said synthesizer comprises circuitry for imposing an adjustable time delay of generation of said false echo with respect to the time of occurrence of said incident acoustic energy.

14. The system of claim 9, wherein:

a) said ultrasonic examination system includes means for coupling said transducer apparatus to said transmitter for a time defining a transmission period, and means for coupling said transducer to said receiver for a subsequent time defining a listening period; and, b) said synthesizer comprises circuitry for returning a plurality of said apparent echoes during said listening period, each apparent echo representing a point of an apparent acoustic image.

15. The system of claim 9, wherein said test transducer apparatus comprises a curved array of individual transducer elements.

16. The system of claim 9, wherein said test transducer apparatus comprises a linear or curved linear transducer element array.

17. The system of claim 9, wherein said test transducer apparatus comprises an annular array.

18. The test system of claim 9, wherein said test transducer array comprises a matrix array.

19. The test system of claim 9, wherein said ultrasonic examination system comprises a Doppler ultrasonic system.

20. The test system of claim 9, wherein said ultrasonic examination system comprises a color flow mapping system.

21. A method for simulating to an ultrasonic imaging system the presence of an acoustic image in a region of the field of the system when in fact no such acoustic image is present in said region, said ultrasonic system including transducer apparatus for propagating pulsed incident ultrasonic energy into said region and for detecting ultrasonic echoes resultant upon incidence of said incident energy upon acoustical interfaces within said region, said method comprising the steps of:

a) operating said ultrasonic imaging system when no acoustical interface is present in said region;

b) detecting the occurrence and characteristics of said incident ultrasonic radiation, including wave shape, frequency, amplitude, pulse length, and pulse rate of said incident ultrasonic radiation;

c) storing said detected information;

d) utilizing said stored information for producing signals representing false ultrasonic echoes resembling echoes which would have been generated from incidence of said incident acoustic energy upon an object, were such an object located within said field.

* * * * *